United States Patent
Yamaguchi

(10) Patent No.: US 8,417,466 B2
(45) Date of Patent: Apr. 9, 2013

(54) MASS ANALYSIS DATA PROCESSING APPARATUS

(75) Inventor: Shinichi Yamaguchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/739,108

(22) PCT Filed: Oct. 22, 2007

(86) PCT No.: PCT/JP2007/001152
§ 371 (c)(1),
(2), (4) Date: May 24, 2010

(87) PCT Pub. No.: WO2009/054024
PCT Pub. Date: Apr. 30, 2009

(65) Prior Publication Data
US 2010/0324833 A1  Dec. 23, 2010

(51) Int. Cl.
G01N 15/00 (2006.01)
G01N 27/00 (2006.01)
G06F 19/00 (2006.01)
G06F 17/40 (2006.01)

(52) U.S. Cl. ........... 702/23; 73/866; 73/866.3; 250/281; 324/464; 702/1; 702/127; 702/187; 702/189; 708/200

(58) Field of Classification Search ............... 73/865.5, 73/865.8, 866, 866.3; 250/281, 282, 283; 324/459, 464; 340/500, 540; 356/335; 702/1, 702/22, 23, 26, 27, 29, 127, 187, 189; 708/100, 708/105, 200
See application file for complete search history.

(56) References Cited

U.S. PATENT DOCUMENTS
2,570,158 A * 10/1951 Schissel .................. 250/282
2,806,143 A * 9/1957 Carter .................... 250/298
(Continued)

FOREIGN PATENT DOCUMENTS
EP    2208990 A1 *  7/2010
JP   61-020856 A     1/1986
(Continued)

OTHER PUBLICATIONS

S. Yamaguchi, et al., Automated Detection of Metabolites for Liquid Chromatography/Mass Spectrometry/Mass Spectrometry Data Using Partial Least Squares with Ion Trap Time of Flight Mass Spectrometry, J. Mass Spectrom. Soc. Jpn., 2007, pp. 83-89, vol. 55, No. 2.

(Continued)

Primary Examiner — Edward Cosimano
(74) Attorney, Agent, or Firm — Sughrue Mion, PLLC

(57) ABSTRACT

A product ion spectrum is created on the basis of $MS^2$ analysis data respectively obtained for a parent compound and a metabolite (S1 and S2). Additionally, a neutral loss spectrum, in which the mass of each product ion is replaced with a mass difference between the mass of the product ion and that of a precursor ion, is created (S3). Then, a common peak having the same mass in both the parent compound and the metabolite is extracted (S4), and a complementary peak appearing at a position corresponding to the difference between the mass of the common peak and that of the precursor ion is extracted (S5); the complementary peak corresponding to a common peak located on the product ion spectrum appears on the neutral loss spectrum, while the complementary peak corresponding to a common peak located on the neutral loss spectrum appears on the product ion spectrum. In the process of displaying the four spectrums in an integrated form, different display colors are assigned to the common peak, complementary peak and other peaks so that the different peaks can be easily distinguished (S6 to S9).

6 Claims, 5 Drawing Sheets

U.S. PATENT DOCUMENTS

| | | | | |
|---|---|---|---|---|
| 2,852,687 | A * | 9/1958 | Kudravetz et al. | 250/281 |
| 2,883,255 | A * | 4/1959 | Anderson | 346/34 |
| 4,008,388 | A * | 2/1977 | McLafferty et al. | 702/27 |
| 6,573,492 | B2 * | 6/2003 | Nagai | 250/282 |
| 6,914,239 | B2 * | 7/2005 | Yoshinari et al. | 250/281 |
| 7,230,235 | B2 * | 6/2007 | Goldberg et al. | 250/288 |
| 7,297,940 | B2 * | 11/2007 | Bern | 250/282 |
| 7,956,320 | B2 * | 6/2011 | Yamaguchi | 250/281 |
| 2001/0007349 | A1 * | 7/2001 | Nagai | 250/281 |
| 2003/0036207 | A1 * | 2/2003 | Washburn et al. | 436/518 |
| 2004/0181347 | A1 * | 9/2004 | Yoshinari et al. | 702/27 |
| 2006/0249667 | A1 * | 11/2006 | Goldberg et al. | 250/281 |
| 2006/0249668 | A1 * | 11/2006 | Goldberg et al. | 250/281 |
| 2006/0249669 | A1 * | 11/2006 | Bern | 250/282 |
| 2007/0187588 | A1 | 8/2007 | Yoshinari et al. | |
| 2009/0230298 | A1 * | 9/2009 | Yamaguchi | 250/281 |
| 2010/0312489 | A1 * | 12/2010 | Yamaguchi | 702/23 |

FOREIGN PATENT DOCUMENTS

| | | |
|---|---|---|
| JP | 03-165445 A | 7/1991 |
| JP | 08-124519 A | 5/1996 |
| JP | 10-142196 A | 5/1998 |
| JP | 10-293120 A | 11/1998 |
| JP | 11-064285 A | 3/1999 |
| JP | 2001-249114 A | 9/2001 |
| JP | 2007-218692 A | 8/2007 |

OTHER PUBLICATIONS

G. Zurek, et al., Novel Strategies for Metabolite Identification Using HPLC-Ion Trap Mass Spectrometry, The Application Notebook, Advertising Supplement, LCGC North America, Jun. 2003, pp. 13-14, 1 page cover sheet.

* cited by examiner

Fig. 3
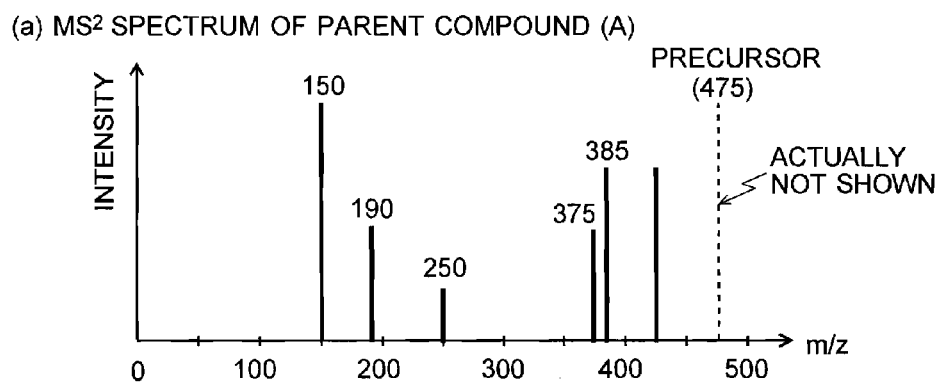
(a) MS² SPECTRUM OF PARENT COMPOUND (A)
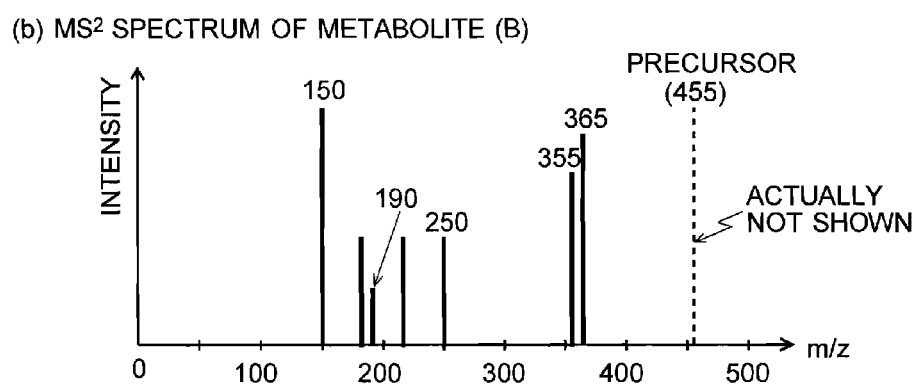
(b) MS² SPECTRUM OF METABOLITE (B)
Fig. 4
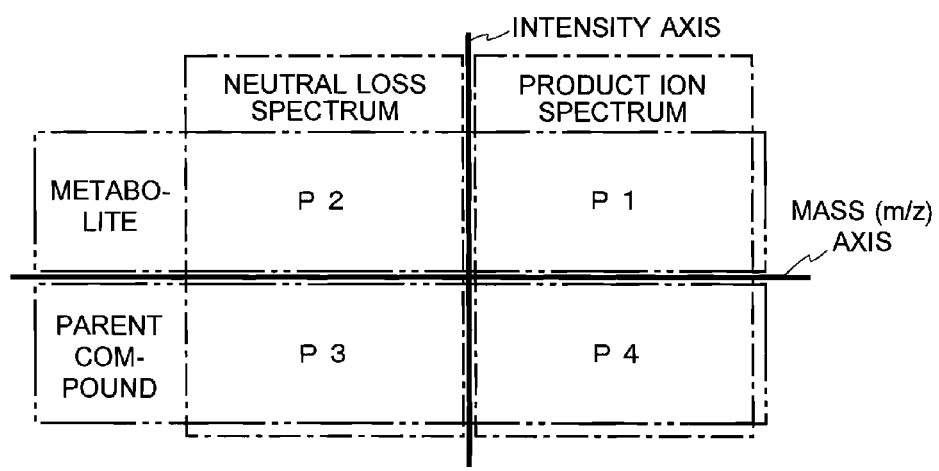

MASS ANALYSIS DATA PROCESSING APPARATUS

TECHNICAL FIELD

The present invention relates to a mass analysis data processing system for processing data obtained by a mass spectrometer capable of an $MS^n$ analysis, where n is an integer greater than one.

BACKGROUND ART

In the field of mass analysis using an ion trap mass spectrometer or other apparatuses, a technique called the MS/MS analysis (or tandem analysis) is conventionally known. In a general MS/MS analysis, an ion having a specific mass (or mass-to-charge ratio, m/z, to be exact) is first selected as a precursor ion from an object to be analyzed. Next, the selected precursor ion is dissociated by a collision induced dissociation (CID) process to produce product ions (also called fragment ions). The resulting product ions are subjected to a mass analysis to obtain information relating to the mass of the product ions, the ions and neutral molecules desorbed by the dissociation operation, and other particles. Based on this information, the composition and chemical structure of the target sample molecule are deduced.

In recent years, samples to be analyzed with this type of system have been progressively increasing in molecular weight and becoming more complex in structure (or the composition). Therefore, depending on the nature of the sample, it is possible that the sample cannot be dissociated into sufficiently small masses by only one stage of the dissociation process. In such a case, an $MS^n$ analysis may be performed, where the dissociation operation is repeated two or more times and the eventually obtained product ions are subjected to mass analysis (for example, refer to Patent Document 1, 2 or other documents). The aforementioned MS/MS analysis is an $MS^n$ analysis where n=2.

In general, mass spectrometers create a mass spectrum ($MS^n$ spectrum), with the horizontal axis indicating the mass-to-charge ratio and the vertical axis indicating the signal intensity (relative intensity), as the result of mass analysis and presents it on a display screen as one of the analysis results. In the case of a mass spectrometer capable of $MS^n$ analyses, a plurality of precursor ions having different masses can be respectively selected, in which case an $MS^n$ spectrum will be obtained for each precursor ion. An $MS^n$ spectrum provides various types of peak information reflecting the state of the molecular bonds of the original compound. Accordingly, a plurality of compounds having similar structures are likely to show $MS^n$ spectrums having similar patterns.

By the way, analyzing metabolites resulting from chemical changes in a living organism is a crucial subject in many fields, such as the diagnosis of various kinds of diseases and illnesses, the assessment of the effectiveness and safety of drugs and functional foods, and the research on lifestyle and health. In recent years, a method called Metabolomics for exhaustively analyzing a metabolite has been attracting attention. In this metabolite analysis, the aforementioned method using $MS^n$ spectrums is useful to search for a compound resulting from a metabolism of another compound having a known structure (this compound will be hereinafter called a "parent compound", and the former compound will be called a "metabolite"). This is due to the fact that a metabolite results from a partial modification in the structure of a parent compound and their $MS^n$ spectrums include many common features. Accordingly, by comparing their $MS^n$ spectrums, it is possible to extract candidates for the metabolite from a large number of compounds. Software programs for automatically performing the analysis process described to this point have been already provided.

However, to achieve the ultimate objective, i.e. the deduction and determination of the structure of a metabolite, an analysis operator needs to visually check $MS^n$ analysis data and other data and make a judgment. Improving the efficiency of this task has been a major challenge to enhance the throughput of the analysis. One reason for the inefficiency of this checking task is that it is difficult to immediately, or intuitively, visually identify the peak that corresponds to the modified portion of the parent compound or metabolite in the $MS^n$ spectrum. Another reason is that, even when it is appropriate to increase the number of stages of the dissociation operation (i.e. to perform the $MS^n$ analysis with a large value of n), it is not easy to decide which peak should be given priority to be the precursor ion for the next stage.

Patent Document 1: Japanese Unexamined Patent Application Publication No. H10-142196

Patent Document 2: Japanese Unexamined Patent Application Publication No. 2001-249114

DISCLOSURE OF THE INVENTION

Problem to be Solved by the Invention

The present invention has been developed to solve the aforementioned problems, and its objective is to provide a mass analysis data processing system capable of providing useful information for performing an analysis of a plurality of components with similar chemical structures, e.g. the deduction of chemical structures, by using $MS^n$ spectrums of the components in question.

Means for Solving the Problems

The present invention aimed at solving the previously described problems is a mass analysis data processing system for processing mass analysis data collected by using a mass spectrometer capable of an $MS^n$ analysis (where n is an integer greater than one), the mass analysis data being obtained by an $MS^n$ analysis on an ion having a specific mass as a precursor ion for each of at least two components inclusive of a first component and a second component, which is characterized by including:

a) an $MS^n$ spectrum creating means for creating an $MS^n$ spectrum based on the mass analysis data obtained for each of the first component and the second component;

b) an $MS^n$ mass-difference spectrum creating means for calculating, for each of the two $MS^n$ spectrums, a mass difference between the mass of each peak among some or all of the peaks appearing on the $MS^n$ spectrum and the mass of the precursor ion, and for creating an $MS^n$ mass-difference spectrum having a peak at each calculated mass difference;

c) a common-peak extracting means for extracting a common peak having the same mass in the two $MS^n$ spectrums relating to the first component and the second component and/or the two $MS^n$ mass-difference spectrums relating to the first component and the second component;

d) a complementary-peak extracting means for extracting a complementary peak on the $MS^n$ spectrum and/or the $MS^n$ mass-difference spectrum relating to the first component and/or the second component, the complementary peak corresponding to a mass difference between the mass of the precursor ion used in the MS" analysis for the first component and/or the second component and the mass of the common peak; and e) a display control means for showing the MS" spectrum and/or the MS" mass-difference spectrum on a display screen, with the complementary peak having a style visually distinguishable from that of the other peaks on the MS" spectrum and/or the MS" mass-difference spectrum relating to the first component and/or the second component.

An example of the mass spectrometer capable of an MS" analysis is an ion-trap mass spectrometer using an ion trap, which is typically a three-dimensional quadrupole ion trap. The dissociation of precursor ions is normally achieved by collision-induced dissociation. However, other methods may be used to dissociate precursor ions.

Any components may be chosen as the first component and the second component. However, applying the present invention to two components having totally different chemical structures will produce no significant results. Therefore, it is practically useful to choose two components having similar chemical structures. For example, given a certain compound as the first component, a metabolite produced from this compound by a metabolism in a living organism or other environments may be chosen as the second component.

The "visually distinguishable" style is represented, for example, by a different color, thickness or type of the line of a peak, or any combination of these properties. Instead of changing the lines of the peaks, it is possible to change the color or other properties of the mass labels numerically showing the mass information or other data of the peaks.

In the present invention, the MS" spectrum is a mass spectrum reflecting the intensity of the product ions (or residual precursor ions that have not been dissociated) actually detected by a detector in the mass spectrometer. By contrast, the MS" mass-difference spectrum changes its meaning depending on the valence of the precursor ion. If the precursor ion is monovalent, the MS" mass-difference spectrum reflects the intensity of neutral molecules that have been desorbed and excluded from the precursor ion by dissociation (neutral loss); therefore, this spectrum can be regarded as a virtual mass spectrum relating to some substances that have not been actually detected. If the precursor ion is multivalent, the MS" mass-difference spectrum reflects the intensity of the desorbed ions that have been actually detected.

For example, the complementary peak on the MS" mass-difference spectrum relating to the first component is the peak that appears at a mass value of Mb−Ma, where Ma is the mass of a common peak on the MS" spectrums relating to the first and second components and Mb is the mass of the precursor ion used in the MS" analysis of the first component (Mb>Ma). On the other hand, the complementary peak on the MS" spectrum relating to the first component is the peak that appears at a mass value of Mb−Mc, where Mc is the mass of a common peak on the MS" mass-difference spectrums relating to the first and second components and Mb is the mass of the precursor ion used in the MS" analysis of the first component (Mb>Mc).

Similarly, the complementary peak on the MS" mass-difference spectrum relating to the second component is the peak that appears at a mass value of Md−Ma, where Ma is the mass of a common peak on the MS" spectrums relating to the first and second components and Md is the mass of the precursor ion used in the MS" analysis of the second component (Md>Ma). On the other hand, the complementary peak on the MS" spectrum relating to the second component is the peak that appears at a mass value of Md−Mc, where Mc is the mass of a common peak on the MS" mass-difference spectrums relating to the first and second components Mc and Md is the mass of the precursor ion used in the MS" analysis of the second component (Md>Mc).

The mass analysis data processing system creates at least four mass spectrums, i.e. the MS" spectrum relating to the first component, the MS" mass-difference spectrum relating to the first component, the MS" spectrum relating to the second component and the MS" mass-difference spectrum relating to the second component. (Each of them is normally in the form of a graph with the horizontal axis indicating the mass and the vertical axis indicating the relative intensity.) It is not always necessary to simultaneously display all of them.

However, it is preferable to simultaneously show all the mass spectrums on the same display screen so that one can at a glance compare the first and second components and recognize the relationship between a common peak and a complementary peak corresponding to it. For that purpose, it is preferable to provide the display control means with the function of determining the arrangement of the MS" spectrum and the MS" mass-difference spectrum relating to the first component as well as the MS" spectrum and the MS" mass-difference spectrum relating to the second component so that all the spectrums will be shown on the same display screen.

For example, the MS" spectrums of the first and second components may be symmetrically arranged with respect to the mass axis. Similarly, the MS" mass-difference spectrums of the first and second components can also be symmetrically arranged with respect to the mass axis. In this case, the common peaks having the same mass extend in an approximately vertical direction, penetrating through the mass axis. Common peaks drawn in this manner are easy to locate.

Effect of the Invention

When the first and second components have similar chemical structures, the common peak that appears on the MS" spectrums or MS" mass-difference spectrums of the two components reflects an ion or neutral molecule present at a portion (chemical structure) common to the first and second components. Conversely, the complementary peak reflects a portion that is not common to the first and second components. In other words, this peak reflects a portion characteristic of, or specific to, either the first or second component. Particularly, in the case where this characteristic portion is desorbed in the form of a neutral molecule by the dissociation of a precursor ion, the peak corresponding to this neutral molecule cannot appear on normal MS" spectrums but will appear on the MS" mass-difference spectrums created by the data processing system according to the present invention. Furthermore, this peak is shown in a special style and can be easily distinguished from the other peaks, so that the analysis operator can at a glance recognize the portion concerned. This will improve the efficiency of the chemical structure analysis.

In the case where the mass corresponding to the complementary peak appearing on the MS" spectrum is still large, it is preferable to proceed to the next n+1-th stage of dissociation operation and perform an $MS^{n+1}$ analysis using an ion corresponding to the complementary peak as the precursor ion. In such a case, the task of setting parameters and commands necessary for the next analysis can be efficiently performed with the data processing system according to the present invention since the complementary peak can be instantaneously located on the MS" spectrum as well.

BRIEF DESCRIPTION OF THE DRAWINGS

FIG. 3 is a diagram showing an example of two $MS^n$ spectrums displayed by the mass analyzing system of the present embodiment.

FIG. 4 is a model diagram for explaining a method of displaying $MS^n$ spectrums by the mass analyzing system of the present embodiment.

EXPLANATION OF NUMERALS

1 ... Mass Analyzer Unit
2 ... Ion Source
3 ... Ion Optical System
4 ... Ion Trap
5 ... Time-of-Flight Mass Separator (TOF)
6 ... Detector
10 ... Central Controller
11 ... Analysis Controller
12 ... Data Processor
13 ... Operation Unit
14 ... Display Unit

BEST MODE FOR CARRYING OUT THE INVENTION

Figure 1:
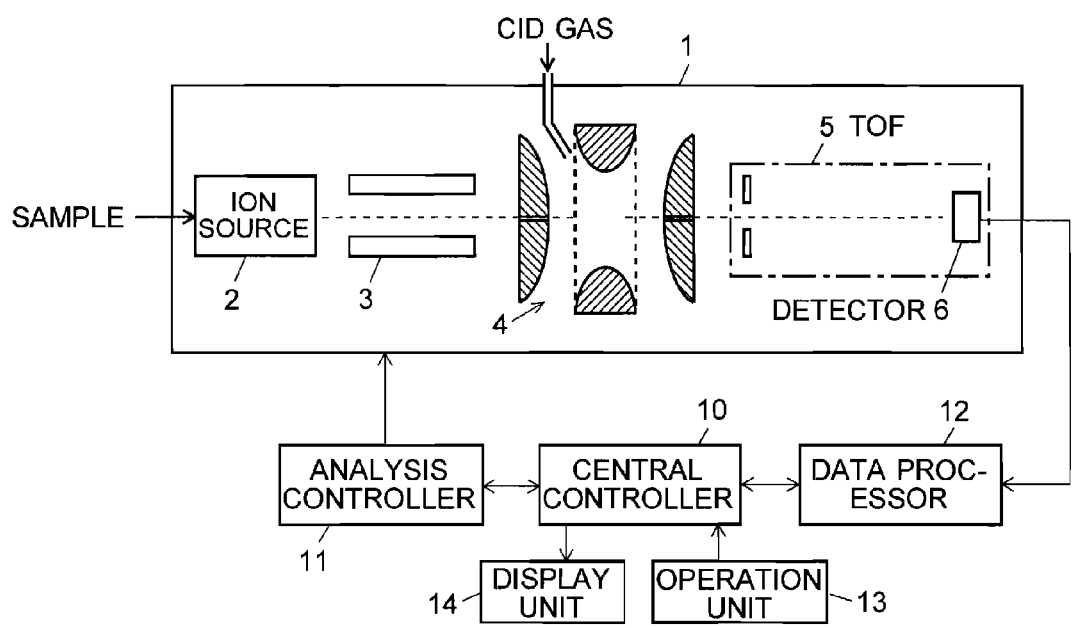
FIG. 1 is an overall configuration diagram of one embodiment of a mass analyzing system including a data processing system according to the present invention.

One embodiment of a mass analyzing system including a data processing system according to the present invention is hereinafter described with reference to the drawings. FIG. 1 is an overall configuration diagram of the present mass analyzing system.

A mass analyzer unit 1 includes an ion source 2 for ionizing sample molecules, a three-dimensional quadrupole ion trap 4 for temporarily storing ions within its internal space and for promoting collision-induced dissociation of these ions, an ion optical system 3 for guiding the ions produced by the ion source 2 to the ion trap 4, a time-of-flight mass separator (TOF) 5 for separating ions emitted from the ion trap 4 according to their mass (or mass-to-charge ratio, m/z, to be exact) and a detector 6 for detecting the ions separated by the TOF 5.

An analysis controller 11 conducts an $MS^n$ analysis by controlling the operation of each component of the mass analyzer unit 1 according to the instructions from a central controller 10. A data processor 12 receives detection signals from the detector 6, converts them into digital data and performs a predetermined data processing inclusive of a display process which will be described later. An operation unit 13 and display unit 14, which constitutes a user interface, are connected to the central controller 10. Most of the functions of the central controller 10, analysis controller 11 and data processor 12 can be embodied by a personal computer with appropriate controlling and processing software programs installed therein.

The basic operation of the mass analyzing system having the previously described configuration is hereinafter schematically described. When an $MS^1$ analysis, i.e. a normal mass analysis with no dissociation operation, is to be performed, the system operates as follows under the control of the analysis controller 11: The ion source 2 ionizes sample molecules to produce various kinds of ions. These ions are then introduced through the ion optical system 3 into the ion trap 4. Within the ion trap 4, the ions are temporarily captured by a quadrupole electric field formed by a radio-frequency voltage applied from a power source (not shown) to the electrodes. Subsequently, at a specific timing, kinetic energy is simultaneously given to all the ions captured in the ion trap 4, whereby the ions are ejected from the ion trap 4 and introduced into the TOF 5. This means that the ion trap 4 corresponds to the start point where the ions begin their flight to the TOF 5. While flying through the flight space inside the TOF 5, the ions are temporally separated according to their mass. The separated ions sequentially arrive at, and are detected by, the detector 6.

The data processor 12 receives this detection signal and converts the time of flight within the TOF 5 to the mass to create a mass spectrum with the horizontal axis indicating the mass and the vertical axis indicating the relative intensity. This mass spectrum is displayed via the central controller 10 on the screen of the display unit 14. Based on this mass-analysis result, the person in charge of the analysis (who is hereinafter called "the analyzer") designates one ion as a precursor ion for an $MS^2$ (MS/MS) analysis including one stage of the dissociation operation.

When the analyzer enters, for example, the mass of the precursor ion through the operation unit 13 and gives a command to carry out the $MS^2$ analysis, the system operates as follows under the control of the analysis controller 11: The ion source 2 ionizes sample molecules to produce various kinds of ions. These ions are then introduced through the ion optical system 3 into the ion trap 4. Within the ion trap 4, the ions are temporarily captured by the aforementioned quadrupole electric field, immediately after which a voltage for dissipating unwanted ions other than the previously selected precursor ion is applied to the electrodes. As a result, only the precursor ion is left within the ion trap 4 (the selection of the precursor ion). Additionally, a CID gas is introduced from an external source. The precursor ion is dissociated due to the collision with the CID gas, whereby various kinds of product ions are produced according to the mode of dissociation.

The product ions produced by the dissociation (and the residual precursor ion, if it remains) are collectively ejected from the ion trap 4 at a predetermined timing and introduced into the TOF 5. As in the case of the normal mass analysis, the ions are temporally separated according to their mass while flying within the flight space of the TOF 5, and the separated ions sequentially arrive at, and are detected by, the detector 6. The data processor 12 receives this detection signal and converts the flight time within the TOF 5 to the mass to create an $MS^2$ spectrum. This $MS^2$ spectrum is displayed via the central controller 10 on the screen of the display unit 14.

It is also possible to perform an $MS^n$ analysis with n=3 or a greater number by repeating the dissociation operation in stages, where one of the product ions produced within the ion trap 4 in one stage of the dissociation process is chosen as a new precursor ion to be dissociated by the CID process. Although there is no theoretical limit on the number of stages of the dissociation operation, the maximum value of n is practically within the range from 3 to 6.

The data processor 12 in the mass analyzing system of the present embodiment performs a characteristic operation when it creates a set of information to be displayed on the display unit 14 after receiving the detection signals obtained by the $MS^n$ analysis. This operation is hereinafter described with reference to FIGS. 2 to 6.

Figure 2:
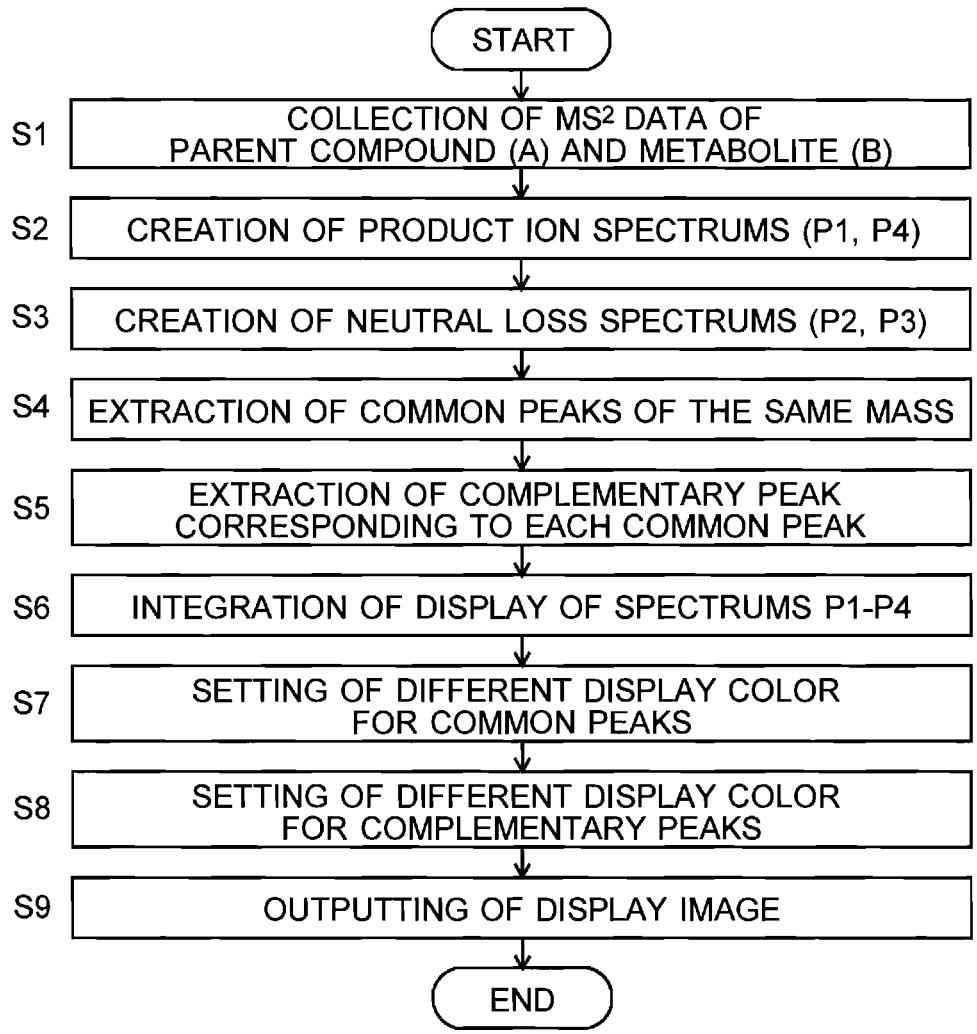
FIG. 2 is a flowchart showing the steps of a spectrum-displaying process performed by the mass analyzing system of the present embodiment.

As one example, the following description deals with the case of the structural analysis of a metabolite (labeled "B")

originating from a parent compound (labeled "A") having a known chemical structure. FIG. 2 is a flowchart showing the steps of a spectrum-displaying process characteristic of the mass analyzing system of the present embodiment.

First, with the mass analyzing system shown in FIG. 1, an $MS^2$ analysis is respectively performed on both the parent compound (A) and metabolite (B) to collect $MS^2$ spectrum data for these compounds (Step S1). In the present example, the mass of the precursor ion used in the $MS^2$ analysis for the parent compound (A) is 475, and that of the precursor ion in the $MS^2$ analysis for the metabolite (B) is 455. FIG. 3 shows examples of the $MS^2$ spectrum of the parent compound (A) and that of the metabolite (B). Although the peak corresponding to the precursor ion in each spectrum does not actually exist, the figure shows this peak by a dotted line for easier understanding of the following description. The $MS^2$ spectrums shown in FIG. 3 illustrate the intensity of the product ions and hence are hereinafter referred to as the "product ion spectrums."

After the data have been collected in the previously described manner, when the data processing is initiated, the data processor 12 creates a product ion spectrum, as shown in FIG. 3, based on each set of the collected data (Step S2). In this step, a peak list, which relates each mass to an intensity, is created. This peak list can be graphically represented to obtain the product ion spectrum, in which the listed peaks are drawn on a graph with the horizontal axis indicating the mass and the vertical axis indicating the intensity.

Next, for the parent compound (A) and the metabolite (B), respectively, the mass difference between the mass of the precursor ion and the mass of each product ion appearing on the product ion spectrum (i.e. listed in the aforementioned peak list) is sequentially calculated for each product ion. Then, a mass-difference peak list, which relates each mass difference to the intensity of the product ion that has been the origin of the mass difference, is created. For example, in the case of FIG. 3 at (a) where the mass of the precursor ion is 475, a product ion having a mass of 150 has a mass difference of 325, and this mass difference is related to the intensity of the peak of the product ion having a mass of 150 and registered in the mass-difference peak list. This operation is similarly performed for each and every peak appearing on the product ion spectrum to complete a mass-difference peak list. A graphical representation of this peak list is the aforementioned $MS^2$ mass-difference spectrum, in which the listed peaks are drawn on a graph with the horizontal axis indicating the mass and the vertical axis indicating the intensity. The mass difference corresponds to the mass of a fragment desorbed from the precursor ion due to the dissociation. On the assumption that the precursor ion is monovalent, the desorbed fragment is a neutral molecule. Accordingly, the $MS^2$ mass-difference spectrum is hereinafter called the "neutral loss spectrum" (Step S3).

By the processes in Steps S2 and S3, the product ion spectrum and neutral loss spectrum relating to the parent compound (A) and those spectrums relating to the metabolite (B) are created. Subsequently, the peak list of the parent compound (A) and that of the metabolite (B) are compared to locate a peak having the same mass and extract this peak as a common peak. The same process is also performed on the mass-difference peak list of the parent compound (A) and that of the metabolite (B) to extract a common peak from both lists (Step S4).

Next, for each of one or more common peaks appearing on the product ion spectrum of the metabolite (B), the mass of a complementary peak to be paired with the common peak in question is calculated. The phrase "to be paired" means that the total of the masses of the common peak and complementary peak should equal the mass of the precursor ion. The mass of the complementary peak to be paired with a given common peak can be obtained by subtracting the mass of the common peak from that of the precursor ion. For example, the peak with a mass of 150 in FIG. 3 at (b) is a common peak and should have the complementary peak located at a mass of 305 on the neutral loss spectrum since subtracting 150 from 455 (i.e. the mass of the precursor ion) comes to 305. The mass of a complementary peak to be paired with each of one or more common peaks appearing on the neutral loss spectrum of the metabolite (B) can also be similarly calculated. After the masses of the complementary peaks are thus calculated, these complementary peaks are extracted from both the peak list and the mass difference peak list (Step S5).

Subsequently, a spectrum display integration process for showing the four spectrums (product ion spectrums and neutral loss spectrums) created in Steps S2 and S3 on the same display screen is performed (Step S6). In the present embodiment, as shown in FIG. 4, the product ion spectrum P1 of the metabolite (B) and the product ion spectrum P4 of the parent compound (A) are symmetrically arranged with respect to the horizontal mass axis, and the neutral loss spectrum P2 of the metabolite (B) and the neutral loss spectrum P4 of the parent compound (A) are also symmetrically arranged with respect to the same horizontal mass axis, with each neighboring pair of the product ion spectrum and neutral loss spectrum being symmetrically arranged with respect to the vertical intensity axis.

Figure 5:
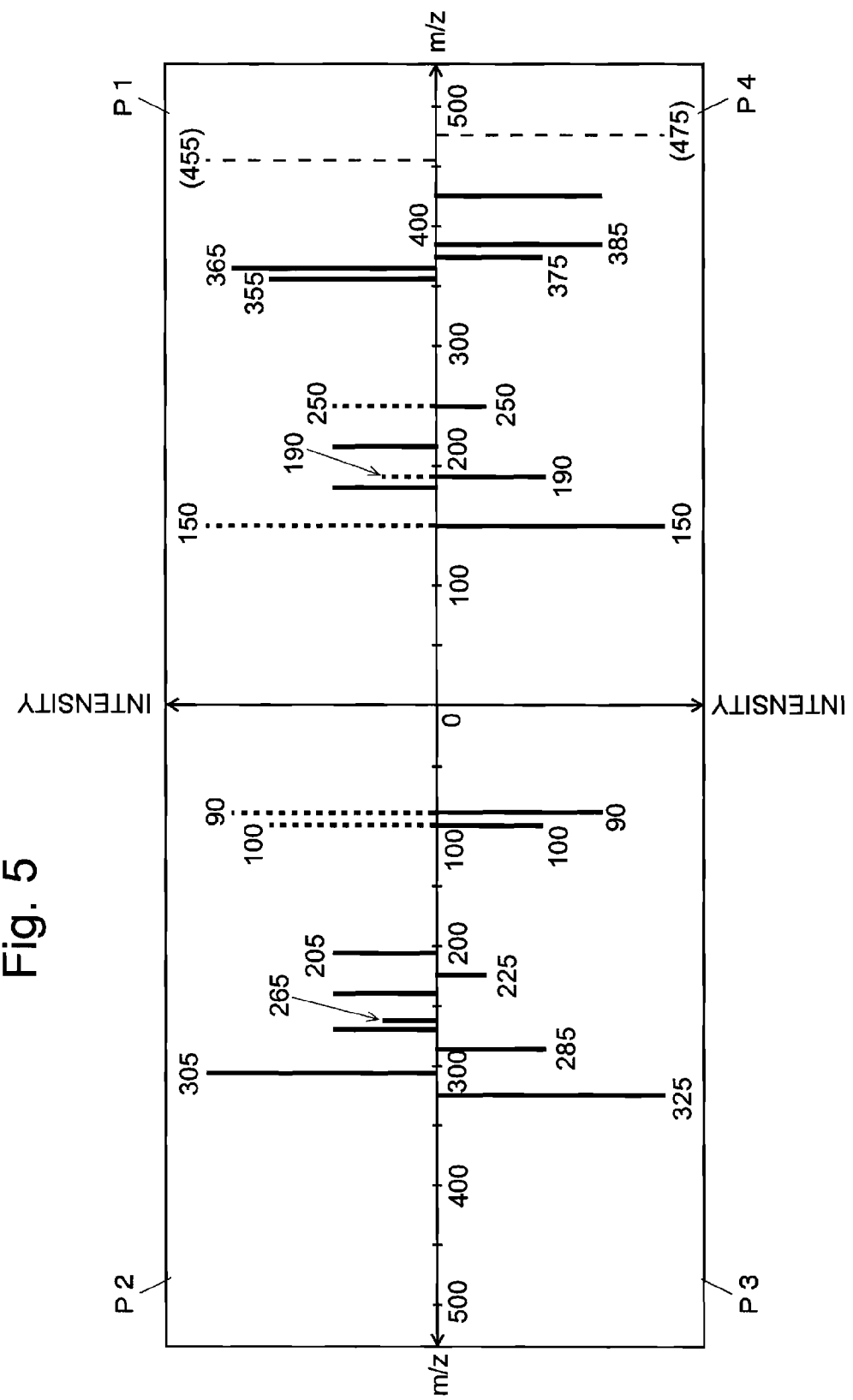
FIG. 5 is a chart for explaining the method of displaying $MS^n$ spectrums by the mass analyzing system of the present embodiment.

FIG. 5 is an example of the display format for integrating the product ion spectrums of the parent compound (A) and the metabolite (B) shown in FIG. 3 as well as the neutral loss spectrums derived from those product ion spectrums. In this example, each common peak is represented by a pair of lines that respectively extend upwards and downwards from the mass axis. In order to highlight the common peaks in both the product ion spectrum and neutral loss spectrum of the metabolite (B), the display color for the common peaks are set so that they are drawn in a color different from the color of the other peaks (Step S7). It should be noted that this difference in color cannot be actually represented in FIG. 5 and the dotted lines are used in the figure to identify the common peaks to be drawn in a different color. As shown, the product ion spectrums have three common peaks at masses of 150, 190 and 250, while the neutral loss spectrums have two, at masses of 90 and 100.

Figure 6:
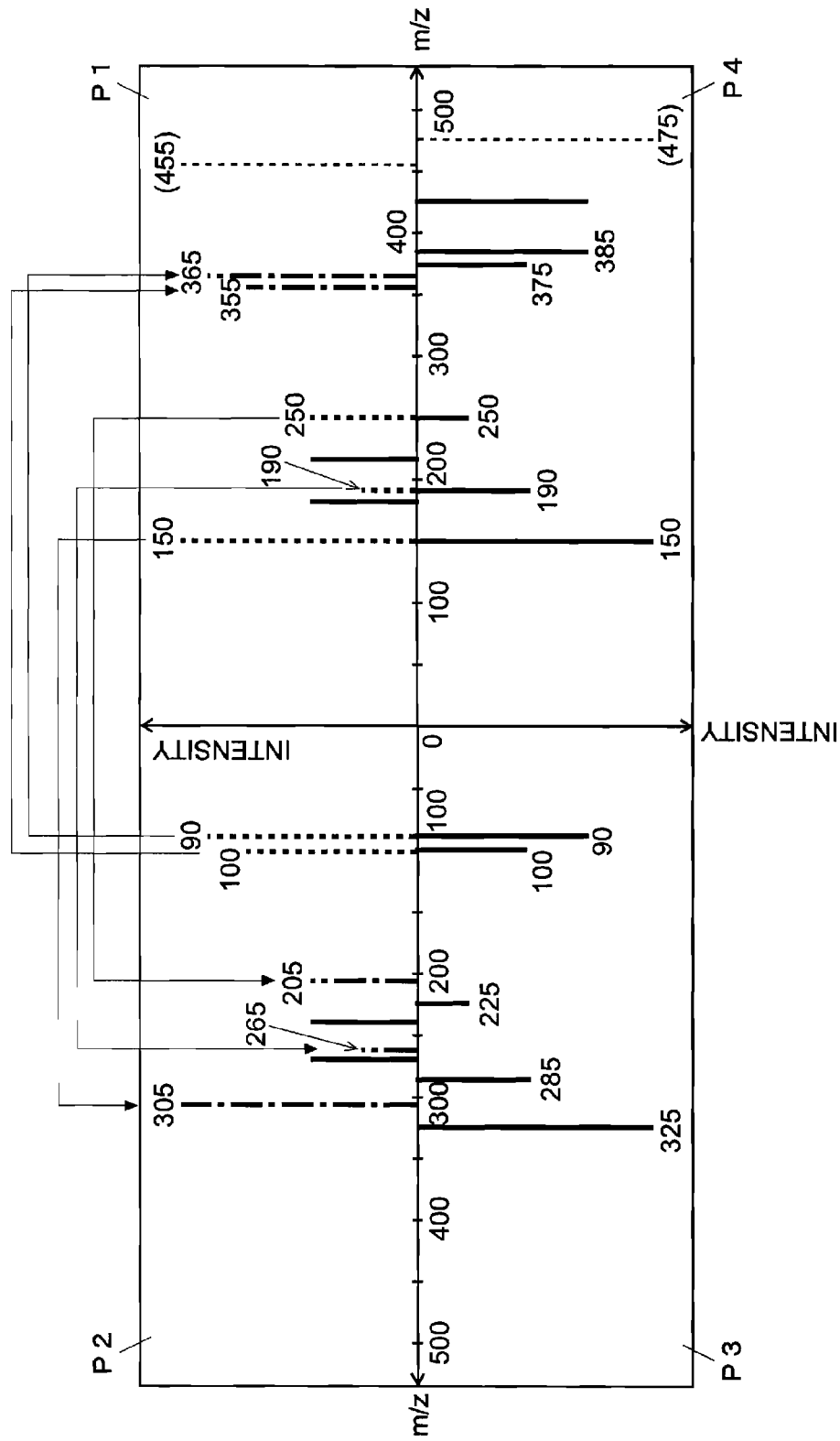
FIG. 6 is a chart for explaining the method of displaying $MS^n$ spectrums by the mass analyzing system of the present embodiment.

Furthermore, in order to highlight the complementary peaks in both the product ion spectrum and neutral loss spectrum of the metabolite (B), the display color for the complementary peaks are also set so that they are drawn in a color different from the color of the other peaks (Step S8). For example, the common peaks may be drawn in red, the complementary peaks in blue, and the other peaks in black. FIG. 6 is an example in which the complementary peaks are also drawn in a different style. It should be noted once more that this difference in style cannot be actually represented in FIG. 6 and the complementary peaks to which the different display color should be applied are drawn in the chained lines. The product ion spectrum has two complementary peaks at masses of 355 and 365, while the neutral loss spectrum has three, at 205, 265 and 305. The arrowed lines, which show the relationships between the common peaks and the complementary peaks, may or may not be actually drawn on the display screen.

The mass spectrums that have been created in an integrated form in Step S6, using the display colors selected in Steps S7 and S8, as shown in FIG. 6, are displayed on the screen of the display unit 14 (Step S9). By viewing this graphical presentation, the analysis operator can easily recognize the common peaks and obtain information relating to the structure common to both the parent compound (A) and the metabolite (B). Additionally, the complementary peaks appearing in the metabolite (B) can also be easily recognized, so that the analyzer can intuitively obtain information relating to the portion characteristics of the metabolite (B), i.e. the site of metabolism. Thus, the task of deducing the chemical structure of the metabolite (B) can be efficiently performed.

The ions corresponding to the complementary peaks appearing on the product ion spectrum of the metabolite (B) still have large masses. Their structure of these ions can be more clarified by further dissociating them into smaller product ions and analyzing the masses of these product ions. Accordingly, it is possible to select one of the ions corresponding to the complementary peaks appearing on the product ion spectrum as the precursor ion for the next, $MS^3$ analysis. This selection of the precursor ion can also be made by the present system.

Other than changing the display color of the peaks, there are many possible methods for highlighting the common peaks and complementary peaks. For example, the line type may be changed, as just shown in FIGS. 5 and 6, or the line thickness may be changed. Instead of the line color of the peaks, the color of the labels indicating the mass values may be changed. Overlaying an additional marker is also possible. In the example of FIGS. 5 and 6, although the display color of the common peaks was changed only in the product ion spectrum and the neutral loss spectrum of the metabolite (B), it is also possible to make a similar change to the product ion spectrum and the neutral loss spectrum of the parent compound (A).

The form of integration of the four mass spectrums is not limited to the one shown in FIG. 4; for example, the four spectrums may be simply aligned in a row. Displaying all the mass spectrums is not always necessary; for example, it is possible to display only the product ion spectrum and the neutral loss spectrum of the metabolite (B) in such a manner that the common peaks and the complementary peaks can be definitely distinguished from the other peaks.

In the previous embodiment, the display process was performed using the result obtained by an $MS^n$ analysis. It is naturally possible to apply the display process to a result obtained by an $MS^3$ analysis, $MS^4$ analysis or other modes of $MS^n$ analysis with n set to any values greater than one.

In actual cases, one parent compound normally produces more than one kind of metabolites. Therefore, it is preferable to create a plurality of display screens for individually comparing the product ion spectrum and neutral loss spectrum of the parent compound to those of the metabolites, with a browsing function for arbitrarily viewing the results relating to the different metabolites by simple operations, such as selecting one of the tabs.

Furthermore, any changes, modifications or additions appropriately made within the spirit of the present invention in any other aspects of the system will naturally fall within the scope of claims of this patent application.

What is claimed is:

1. A mass analysis data processing system for processing mass analysis data collected by using a mass spectrometer capable of an $MS^n$ analysis (where n is an integer greater than one), the mass analysis data being obtained by an $MS^n$ analysis on an ion having a specific mass as a precursor ion for each of at least two components inclusive of a first component and a second component, which is characterized by comprising:

a) an $MS^n$ spectrum creating means for creating an $MS^n$ spectrum based on mass analysis data obtained for each of the first component and the second component;

b) an $MS^n$ mass-difference spectrum creating means for calculating, for each of the two $MS^n$ spectrums, a mass difference between a mass of each peak among some or all of peaks appearing on the $MS^n$ spectrum and a mass of the precursor ion, and for creating an $MS^n$ mass-difference spectrum having a peak at each calculated mass difference;

c) a common-peak extracting means for extracting a common peak having a same mass in the two $MS^n$ spectrums relating to the first component and the second component and/or the two $MS^n$ mass-difference spectrums relating to the first component and the second component;

d) a complementary-peak extracting means for extracting a complementary peak on the $MS^n$ spectrum and/or the $MS^n$ mass-difference spectrum relating to the first component and/or the second component, the complementary peak corresponding to a mass difference between the mass of the precursor ion used in the $MS^n$ analysis for the first component and/or the second component and the mass of the common peak; and e) a display control means for showing the $MS^n$ spectrum and/or the $MS^n$ mass-difference spectrum on a display screen, with the complementary peak having a style visually distinguishable from that of other peaks on the $MS^n$ spectrum and/or the $MS^n$ mass-difference spectrum relating to the first component and/or the second component.

2. The mass analysis data processing system according to claim 1, which is characterized in that the display control means is provided with a function of determining an arrangement of the $MS^n$ spectrum and the $MS^n$ mass-difference spectrum relating to the first component as well as the $MS^n$ spectrum and the $MS^n$ mass-difference spectrum relating to the second component so that all the spectrums will be shown on the same display screen.

3. The mass analysis data processing system according to claim 2, which is characterized in that the $MS^n$ spectrums of the first and second components are symmetrically arranged with respect to the mass axis, and the $MS^n$ mass-difference spectrums of the first and second components are also symmetrically arranged with respect to the mass axis.

4. The mass analysis data processing system according to claim 1, which is characterized in that the visually distinguishable style is represented by a different color, thickness or type of a line of the peak.

5. The mass analysis data processing system according to claim 4, which is characterized in that the display control means is provided with a function of determining an arrangement of the $MS^n$ spectrum and the $MS^n$ mass-difference spectrum relating to the first component as well as the $MS^n$ spectrum and the $MS^n$ mass-difference spectrum relating to the second component so that all the spectrums will be shown on the same display screen.

6. The mass analysis data processing system according to claim 5, which is characterized in that the $MS^n$ spectrums of the first and second components are symmetrically arranged with respect to the mass axis, and the $MS^n$ mass-difference spectrums of the first and second components are also symmetrically arranged with respect to the mass axis.

* * * * *